US007846711B2

(12) United States Patent
Boettner et al.

(10) Patent No.: US 7,846,711 B2
(45) Date of Patent: Dec. 7, 2010

(54) ***LACTOBACILLUS* STRAINS AND USES THEREOF**

(75) Inventors: Mewes Boettner, Berlin (DE); Eckhard Budde, Berlin (DE); Christine Lang, Berlin (DE); Martin Ryser, Berlin (DE); Markus Veen, Berlin (DE)

(73) Assignee: Organobalance GmbH, Berlin (DE)

( * ) Notice: Subject to any disclaimer, the term of this patent is extended or adjusted under 35 U.S.C. 154(b) by 125 days.

(21) Appl. No.: 11/645,363

(22) Filed: Dec. 22, 2006

(65) Prior Publication Data

US 2007/0148149 A1 Jun. 28, 2007

(30) Foreign Application Priority Data

Dec. 22, 2005 (DE) .................. 10 2005 062 731

(51) Int. Cl.
*C12N 1/20* (2006.01)
*A01N 63/00* (2006.01)
(52) U.S. Cl. ................... 435/252.9; 424/93.45
(58) Field of Classification Search ........................ None
See application file for complete search history.

(56) References Cited

U.S. PATENT DOCUMENTS

| 5,716,615 | A | 2/1998 | Vesely et al. ............... 424/93.4 |
| 6,596,530 | B1 * | 7/2003 | Kimura et al. ............ 435/252.9 |
| 2005/0186190 | A1 | 8/2005 | De Simone ............... 424/93.45 |

FOREIGN PATENT DOCUMENTS

| WO | WO 02/053706 A1 | 7/2002 |
| WO | WO 2004/031368 A1 | 4/2004 |
| WO | WO 2004/087891 A1 | 10/2004 |
| WO | WO 2005/060937 A1 | 7/2005 |

OTHER PUBLICATIONS

Bergonzelli et al. Infection and Immunity. Jan. 2006, vol. 74, No. 1, pp. 425-434.*
Kuan-Yuan Wang et al., "Effects of ingesting *Lactobacillus-* and *Bifidobacterium*-containing yogurt in subjects with colonized *Helicobacter pylori*[1-3]", *American Journal of Clinical Nutrition*, vol. 80, 2004, pp. 737-741.
C. Felley et al., "Probiotics and *Helicobacter pylori*", *Best Practice & Research Clinical Gastroenterology*, vol. 17, No. 5, 2003, pp. 785-791.
Immacolatta Alessia Cazzato et al., "Role of probiotics in *Helicobacter pylori* infections", *Scandinavian Journal of Nutrition*, vol. 48, No. 1, 2004, pp. 26-31.
D. Sgouras et al., "In Vitro and In Vivo Inhibition of *Helicobacter pylori* by *Lactobacillus casei* Strain Shirota", *Applied and Environmental Microbiology*, vol. 70, No. 1, Jan. 2004, pp. 518-526.
Marie-Helene Coconnier et al., "Antagonistic Activity against *Helicobacter* Infection In Vitro and In Vivo by the Human *Lactobacilllus acidophilus* Strain LB", *Applied and Environmental Microbiology*, vol. 64, No. 11, Nov. 1998, pp. 4573-4580.

* cited by examiner

*Primary Examiner*—Vera Afremova
(74) *Attorney, Agent, or Firm*—Ann W. Wieczorek; Mayer & Williams PC

(57) ABSTRACT

The invention concerns new isolated *Lactobacillus* cells, which are capable to aggregate *Helicobacter pylori* under culture conditions of the human digestive tract, in particular of the stomach, and to the uses of such cells.

20 Claims, 1 Drawing Sheet

LACTOBACILLUS STRAINS AND USES THEREOF

FIELD OF THE INVENTION

The invention concerns new *Lactobacillus* strains and the uses thereof, in particular for pharmaceutical and/or dietetic compositions.

BACKGROUND OF THE INVENTION

Probiotic microorganisms comprise living or viable cells, which, in their living form, show advantageous effects in human or animal bodies. Probiotic compositions contain such microorganisms. Advantageous effects may in particular be the improvement of the microflora of the digestive tract. In particular, undesired other microorganisms can be inhibited in the microflora by immediate interactions between the probiotic microorganisms and the undesired microorganisms, by immediate interactions due to inhibitions of the metabolism of the undesired microorganism by expression products of the probiotic microorganism, or by intensification of the natural immune system. In general, it is assumed that a main mechanism is the competitive settlement of the gastrointestinal tract, whereby undesired microorganisms cannot settle anymore on the mucosa to a disturbing extent or are displaced.

A group of probiotic microorganisms is for instance formed by *Lactobacillus* strains. These are typically gram-positive, microaerophilic or anaerobic bacteria fermenting sugar with the generation of acids, in particular of lactic acid.

From the document U.S. Pat. No. 5,716,615, a pharmaceutical composition is known in the art, which amongst others contains *Lactobacilli*. This pharmaceutical composition can be used, amongst others, for the treatment of diseases of the gastrointestinal tract.

From the document US 2005/0186190 A1, a dietetic or pharmaceutical composition is known in the art, which contains sphingomyelinase or *lactobacilli* containing sphingomyelinase. This composition is suitable for treatments of infections with *Heliobacter pylori*.

From the document WO 2004/087891, *Lactobacillus* strains are known in the art, which are suitable for the production of pharmaceutical or dietetic compositions for the treatment of infections of the gastrointestinal tract with *Helicobacter pylori*.

From the document WO 2005/060937 A1, tablet-shaped formulations are known in the art, which contain viable *Lactobacillus* cells. These are suitable for the oral administration and treatment of infections of the gastrointestinal tract with pathogens.

From the document WO 2004/031368 A1, *Lactobacillus* strains are known in the art, which are suitable for the treatment of inflammations, which are associated with an infection with *Helicobacter pylori*.

Interactions of *lactobacilli* with *Helicobacter pylori* are further known in the art from the documents Wang et al., Am. J. Clin. Nutr. 80:737-41 (2004); Felley et al., Best Practice & Research Clinical Gastroenterology 17(5):785-791 (2003); Cazzato et al., Scandinavian Journal of Nutrition 48(1):26-31 (2004); and Sgouras et al., Applied and Environmental Microbiology 70(1):518-526 (2004).

*Helicobacter pylori* is a spiral-shaped bacterium colonizing the stomach, and by means of production of urease the pH value in the stomach is increased, and thus the bacteria are protected against the stomach acid. The bacteria penetrate the mucosa and deposit at epithelial cells of the stomach. Such an infection activates the body-own immune system, but the immune response is not sufficiently effective for eliminating the infection, with the consequence of an intensifying immune response. Finally, a chronic inflammation and illness with gastritis or stomach ulcers will occur. Up to now, it is not yet known, by means of which mechanisms *Helicobacter pylori* resists to the immune system.

About the effective mechanisms of the prior art *Lactobacillus* strains against *Helicobacter pylori*, various theories are presented in the above documents. Safe findings about the mechanisms do not exist, however.

Overall, it is desirable to develop *Lactobacillus* strains, which keep the *Helicobacter pylori* cell count in the stomach very low, and which are otherwise free from physiological side effects.

TECHNICAL OBJECT OF THE INVENTION

It is therefore the technical object of the invention to provide *Lactobacillus* strains, which inhibit the settlement of *Helicobacter pylori* on the stomach mucosa.

Further, it is the technical object of the invention to provide dietetic and/or pharmaceutical compositions, which are highly effective in particular in the prophylaxis of a *Helicobacter pylori* infection.

DETAILED DESCRIPTION

Figure 1:
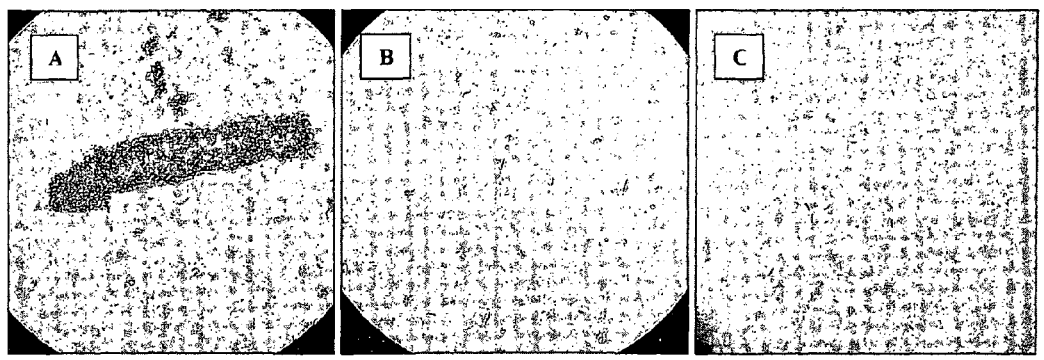
FIG. 1A is a micrograph showing an aggregate of *Helicobacter pylori* by *Lactobacillus* strain DSM 17647.
FIG. 1B is a micrograph showing *Lactobacillus* strain DSM 17648 alone.
FIG. 1C is a micrograph showing *Helicobacter pylori* alone. The magnification for FIGS. 1A-1C is 1,000.

For achieving this technical object, the invention teaches isolated, preferably viable *Lactobacillus* cells, which are capable to aggregate *Helicobacter Pylori* under culture conditions of the human digestive tract, in particular of the stomach.

The invention is based on the surprising perception that certain selected *Lactobacillus* strains are capable of binding to free *Helicobacter pylori* to form aggregates. These relatively large aggregates are not capable anymore of penetrating the mucosa, and consequently *Helicobacter pylori* bacteria can no longer reach and infect die epithelial cells of the stomach. At last, the chronic inflammatory reaction of the immune system is not activated anymore, and an illness with gastritis or stomach ulcers is reliably prevented. The aggregates pass through the gastrointestinal tract and leave the body in a natural way. Even with an infection having occurred already, this mechanism of action of *Lactobacillus* strains according to the invention is helpful, since another infection with additional *Helicobacter pylori* bacteria is prevented and thus the existing infection can more easily be controlled by killing the present *Helicobacter pylori* bacteria. Usually, this is even possible for the natural immune system of the diseased person. In addition, *Lactobacillus* strains according to the invention are presumably also capable of inhibiting the urease activity of *Helicobacter pylori*, such that the *Helicobacter*

*pylori* bacteria in the aggregates lose their protection against the attack of stomach acid. Insofar, a synergistic effect is also achieved.

The essential culture conditions of the human stomach tract comprise a pH value in the range from 1.8 to 4.5 and the presence of pepsin and NaCl. A reference medium, which is characteristic for such culture conditions, comprises the following components: water, 5 g/l NaCl and 3 g/l pepsin, and the pH value is adjusted to 2.0 by means of HCl.

The term aggregation denotes the generation of cell aggregates having a size of at least 1 μm to 1,000 μm and more, comprising *Lactobacillus* cells and *Helicobacter pylori* cells, in suspensions, for instance according to the following examples, in particular in a reference medium, as described above.

For the purpose of the invention, various *Lactobacillus* strains were examined for their ability to aggregate *Helicobacter pylori*, and the following strains were identified and filed as strains according to the invention at the DSMZ Deutsche Sammlung von Mikroorganismen und Zellkulturen GmbH, Mascheroder Weg 1b, D-38124 Braunschweig, Germany: DSM 17646, DSM 17647, DSM 17648, DSM 17649, DSM 17650, DSM 17651, DSM 17652 and DSM 17653. DSM 17646, DSM 17649, DSM 17652 and DSM 17653 are *Lactobacillus brevis* strains. DSM 17647, DSM 17648 and DSM 17651 are *Lactobacillus fermentum* strains. DSM 17650 is a *Lactobacillus pentosus* strain.

The invention further concerns a pharmaceutical and/or dietetic composition comprising a physiologically effective dose of preferably viable *Lactobacillus* cells according to the invention and to a physiologically tolerated carrier. Pharmaceutical compositions are compositions, which serve for therapeutic or prophylactic purposes only, and wherein besides the effective agent only auxiliary and/or carrier substances being usual in galenics are present. Dietetic compositions are compositions, which comprise, besides the effective agent, also food materials and nutritional supplements.

The invention further concerns the use of preferably viable *Lactobacillus* cells according to the invention for the production of a pharmaceutical or dietetic composition, in particular for the prophylaxis and/or treatment of diseases caused by infection with *Helicobacter pylori*, for instance gastrointestinal diseases. To these belong in particular gastritis, stomach ulcers and stomach cancers.

A pharmaceutical composition according to the invention may for instance be characterized by that it contains $10^2$ to $10^{15}$, preferably $10_6$ or $10^8$ to $10^{12}$, in particular $10^8$ to $10^{10}$, *Lactobacillus* cells. Reference value is a unit of administration, for instance a tablet. Preferably, the composition is prepared for the oral administration. The *Lactobacillus* cells are suitably lyophilized.

The galenic preparation of a pharmaceutical composition according to the invention can be made in a way being usual in this technology. Suitable solid or liquid galenic preparation forms are for instance granulates, powders, dragees, tablets, (micro) capsules, suppositories, syrups, juices, suspensions or emulsions, for the production of which usual means are used, such as carrier substances, explosives, binding, coating, swelling, sliding or lubricating agents, tasting agents, sweeteners and solution mediators. As auxiliary substances are named here magnesium carbonate, titanium dioxide, lactose, mannite and other sugars, talcum, milk protein, gelatin, starch, cellulose and derivatives, animal and vegetable oils such as cod-liver oil, sunflower oil, peanut oil or sesame oil, polyethylene glycols and solvents, such as sterile water and mono or multi-valent alcohols, for instance glycerin. A pharmaceutical composition according to the invention can be produced by that cells of at least one *Lactobacillus* strain used according to the invention is mixed in a defined dose with a pharmaceutically suitable and physiologically well tolerated carrier and possibly further suitable active, additional or auxiliary substances, and is prepared in the desired form of administration. Carriers are in particular substances, which are selected from the group comprising "maltodextrin, microcrystalline cellulose, starch, in particular corn starch, levulose, lactose, dextrose, and mixtures of such substances". The composition may contain 0.1 to 95% by weight carrier and 5 to 99.9% by weight lyophilized *Lactobacillus* cells, relative to the total amount of cells and carriers, or consist thereof.

In the case of the dietetic composition, it may be provided that the composition contains $10^2$ to $10^{15}$, preferably $10^6$ to $10^9$, in particular $10^7$ to $10^9$, *Lactobacillus* cells. Reference value is a unit of administration, for instance a packing unit of a food material to be sold to an end user. The physiologically tolerated carrier will normally be a food material, which in particular is selected from the group comprising "milk products, fermented milk products, milk, yogurt, cheese, cereals, muesli bars, and children food preparations".

The invention further concerns a method for the production of a pharmaceutical and/or dietetic composition according to the invention, wherein the lyophilized or not lyophilized, preferably viable *Lactobacillus* cells are mixed with the physiologically tolerated carrier and prepared for oral administration.

Finally, the invention concerns a method for the prophylaxis or treatment of a person that suffers from a disease caused by an *Helicobacter pylori* infection, in particular gastritis or stomach ulcer, or is suspected to fall ill with such a disease, wherein a physiologically effective dose of a pharmaceutical and/or dietetic composition according to the invention is administered to the person one to five times per day. The administration may be performed over a limited time, for instance 1 to 30 weeks, or be unlimited in time. In particular, the latter is suitable for a permanent prophylaxis, also as a preventive against relapse diseases.

In the following, the invention will be explained in more detail based on examples representing embodiments only.

EXAMPLE 1

Storage of Used Strains

The storage of the *Lactobacillus* strains took place in a frozen state. 1 ml of a culture cultivated to a stationary phase ($OD_{600}$/ml 4-8) in MRS medium (55 g/l, pH 6.5; Difco, USA) was mixed with 500 μl of a 50% by volume sterile glycerin solution, and the mixture was deep-frozen to −80° C.

The storage of *Helicobacter pylori* took place in a frozen state. 1 ml of a culture cultivated to a stationary phase in Brucella broth (28 g/l, pH 7.0; BD, USA), supplemented with 5% by volume defillibrated horse blood (Oxoid) was mixed with 500 μl of a 50% by volume sterile glycerin solution, and the mixture was deep-frozen to −80° C. The horse blood was frozen before use and decomposed at 20° C., in order to destroy blood cells.

EXAMPLE 2

Aggregation of *Helicobacter pylori* by *Lactobacillus* Strains According to the Invention The cultivation of the *Lactobacilli* took place in closed Falcon tubes in MRS medium at 37° C. for 24-48 h.

*Helicobacter pylori* was cultivated for 5 to 6 days in an Erlenmeyer flask under microaerophilic conditions and otherwise as described in Example 1.

After the cultivation, the cell morphology was investigated by microscope. Assays were made with cultures consisting of cells with a sigmoidal morphology as well as of cells with coccoidal morphology. Cultures with mixed morphology were also investigated.

The respective cells were harvested by centrifugation at 3,200 g for 10 min, and the supernatant was removed. The cells were washed once in 5 ml buffer and resuspended in 5 ml buffer (PBS buffer containing 1.5 g/l $Na_2HPO_4*2H_2O$, 0.2 g/l $KH_2PO_4$ and 8.8 g/l NaCl). The pH value was adjusted with HCl to 7.0. The $OD_{600}$ value was measured and adjusted to 2 by addition of buffer.

2.5 ml of every cell suspension thus obtained (*Heliobacter pylori/Lactobacillus*) were mixed, and the mixture was vortexed for 10 min. The result was investigated by microscope. Control experiments for self-aggregation were performed by separate investigation of cultures with *Lactobacillus* and *Helicobacter pylori* alone, respectively.

In FIG. 1a suspension with a mixture of *Lactobacillus* and *Helicobacter pylori* can be seen where large aggregates have been formed, whereas such aggregates are absent in the control experiments. This result is obtained for all strains according to the invention, in the FIG. 1, the *Lactobacillus* strain DSM 17648 only is shown in an exemplary manner.

FIG. 1A shows a typical aggregate of *Helicobacter pylori* by the strain DSM 17647. FIG. 1B shows the strain DSM 17648 alone. FIG. 1C shows *Helicobacter pylori* alone. The magnification is 1,000. The aggregates typically have a size of 1 µm, usually from 5 µm to 50 µm, or, as in FIG. 1A, even to 1,000 µm and more (largest extension).

In principle, *Lactobacillus* strains in question can be investigated by means of such an aggregation test for whether the investigated strain induces such an aggregation from *Lactobacillus* and *Helicobacter pylori*.

EXAMPLE 3

Simulation of the Conditions of the Stomach Tract

For the simulation of the in vivo conditions, the experiments of Example 2 were repeated, the resuspension of the *Lactobacillus* cells took place in simulated stomach juice (5 g/l NaCl and 3 g/l pepsin (Sigma)). The pH was adjusted with HCl to 2. This incubation was performed for 30 min at 37° C. Since *Helicobacter pylori* can increase the pH value in the immediate neighborhood of the cells to pH 4, the cells were harvested, as described in Example 2, and then resuspended in acetate buffer pH 4. For adjustment of the buffer, 41 ml of a solution with 0.1 mole/l acetic acid with a solution with 0.2 Mol/l sodium acetate were adjusted to pH 4. Water was then used to fill up to a final volume of 100 ml.

The *Helicobacter pylori* cells were cultivated according to Example 2.

Figure 2:
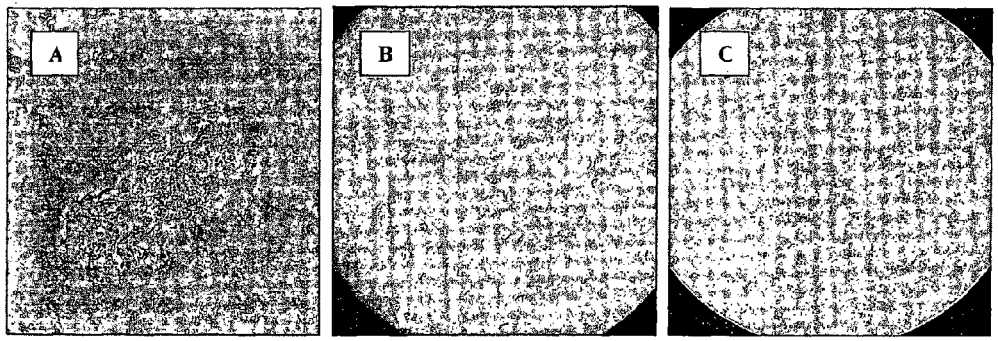
FIG. 2A is a micrograph showing an aggregate of *Helicobacter pylori* by *Lactobacillus* strain DSM 17648 after a simulated stomach passage.
FIG. 2B is a micrograph showing *Lactobacillus* strain DSM 17648 alone after a simulated stomach passage.
FIG. 2C is a micrograph showing *Helicobacter pylori* alone. The magnification for FIGS. 2A-2C is 1,000.

After harvesting the cells according to Example 2, the cells were, different from Example 2, resuspended in an acetate buffer (see above). Thereafter, the aggregation experiments according to Example 2 were performed. The results are shown in FIG. 2. FIG. 2A shows a typical aggregate of *Helicobacter pylori* by the strain DSM 17648 after a simulated stomach passage. FIG. 2B shows strain DSM 17648 alone after a simulated stomach passage. FIG. 2C shows *Helicobacter pylori* alone. The magnification is 1,000. It can be seen that the size of the aggregates obtained in the mixture is in the range from 2 µm to 1,000 µm and more.

This variant, too, of an aggregation test is suitable for identifying *Lactobacillus* strains according to the invention.

EXAMPLE 4

Effect of the Lyophilization of *Lactobacillus*

The bacteria were drawn according to Example 1. Aliquots of 1 ml of the *Lactobacillus* cultures were harvested by centrifugation at 3,200 g for 10 min. The supernatant was removed, and the pellets were lyophilized for 2 h under vacuum. Pellets thus obtained of each of the *Lactobacillus* strains according to the invention were resuspended in 1 ml PBS buffer, pH 7.0. The resuspended *Lactobacillus* cells were mixed in a volume ratio of 1:1 with freshly drawn *Helicobacter pylori* cultures, and the aggregation was determined as in Examples 2 and 3. The capability of the *Lactobacillus* cells to induce an aggregation of *Helicobacter pylori*, was not affected by the lyophilization, as shown by investigations according to the above examples (a photographic documentation was however not made).

EXAMPLE 5

Determination of the Species

The taxonomic determination of the *Lactobacillus* strains according to the invention was performed by using the hydrocarbon fermentation patterns thereof. This was determined by using the API 50 CH system (bioMerieux, France), and the analysis was made with the APILAB PLUS software (Release 3.3.3 of the same supplier). The determination was performed according to supplier's instructions.

EXAMPLE 6

Production of a Pharmaceutical Composition by Using *Lactobacillus* Strains According to the Invention Cells of a *Lactobacillus* strain or of several *Lactobacillus* strains according to the invention are drawn as in Example 4, and were lyophilized. Then, the pellet is ground to a particle size of maximum approx. 1 mm diameter. The obtained granulate is mixed in the following ratios (% by weight) with carrier or auxiliary substances:

20% granulate
2% silicon dioxide (Syloid AL-IFP, GRACE Davidson)
1% magnesium stearate (MF-2-V, Ackros)
77% microcrystalline cellulose (Avicel PH 112, FMC)

Mixing was performed in a Quintech Micromixer at position 70 level II. All components are added at the same time. Mixing is made for approx. 120 s. Then, the obtained mixture is pressed in a commercial tablet press under standard conditions, however with a pressure force as low as possible (<10 kN) so to form tablets having a weight of approx. 500 mg. Every tablet contains approx. $10^8$ to $10^{10}$ *Lactobacillus* cells.

EXAMPLE 7

Production of a Dietetic Composition by Using *Lactobacillus* Strains According to the Invention Cells of a *Lactobacillus* strain or of several *Lactobacillus* strains according to the invention are drawn as in Example 4, and are lyophilized. Lyophilisate containing approx. $10^7$ to $10^8$ *Lactobacillus* cells is respectively mixed with 1 l commercial pasteurized milk and shortly homogenized at 5° C. The homogenized milk is then bottled and packed in a conventional manner.

The invention claimed is:

1. Isolated *Lactobacillus* cells, which are capable of aggregating to *Helicobacter pylori* under culture conditions of the human digestive tract wherein the cells belong to one of the strains DSM 17646, DSM 17647, DSM 17648, DSM 17649, DSM 17650, DSM 17651, DSM 17652 or DSM 17653.

2. A pharmaceutical composition and/or dietetic composition comprising a physiologically effective dose of *Lactobacillus* cells according to claim 1 and a physiologically tolerated carrier.

3. The pharmaceutical composition of claim 2, wherein the composition contains $10^2$ to $10^{15}$ *Lactobacillus* cells.

4. The pharmaceutical composition of claim 2, wherein the composition is prepared for oral administration.

5. The pharmaceutical composition of claim 2, wherein the *Lactobacillus cells are lyophilized.*

6. The pharmaceutical composition of claim 2, wherein the carrier is selected from the group consisting of maltodextrin, microcrystalline cellulose, starch, corn starch, levulose, lactose, dextrose, and mixtures of said carriers.

7. The pharmaceutical composition of claim 2, wherein the composition contains 0.1 to 95% by weight carrier and 5 to 99.9% by weight lyophilized *Lactobacillus* cells.

8. The dietetic composition of claim 2, wherein the composition contains $10^2$ to $10^{15}$ *Lactobacillus* cells.

9. The dietetic composition of claim 2, wherein the physiologically tolerated carrier is a food material.

10. A method for producing a pharmaceutical and/or dietetic composition of claim 5, comprising mixing a physiologically effective quantity of the lyophilized *Lactobacillus* cells with the physiologically tolerated carrier and preparing the composition for oral administration.

11. A method for preventing and/or treating a person who suffers from a disease caused by a *Helicobacter pylori* infection or is suspected to fall ill with a disease caused by a *Helicobacter pylori* infection, comprising administering to the person a physiologically effective dose of a pharmaceutical and/or dietetic composition of claim 2 one to five times per day.

12. Isolated *Lactobacillus* cells of claim 1 which are capable of inhibiting the urease activity of *Helicobacter pylori*, wherein the pylori bacteria in the aggregates lose the ability to protect against the attack of stomach acid.

13. Isolated *Lactobacillus* cells according to claim 1, wherein the culture conditions are culture conditions of the stomach.

14. The pharmaceutical composition of claim 3, wherein the composition contains $10^6$ to $10^{12}$ *Lactobacillus* cells.

15. The pharmaceutical composition of claim 3, wherein the composition contains $10^8$ to $10^{12}$ *Lactobacillus* cells.

16. The pharmaceutical compositions of claim 3, wherein the composition contains $10^8$ to $10^{10}$ *Lactobacillus* cells.

17. The dietetic composition of claim 8, wherein the composition contains $10^6$ to $10^9$ *Lactobacillus* cells.

18. The dietetic composition of claim 8, wherein the composition contains $10^7$ to $10^9$ *Lactobacillus* cells.

19. The dietetic composition of claim 9, wherein the food material is selected from the group comprising milk products, fermented milk products, milk, yogurt, cheese, cereals, muesli bars, and children food preparations.

20. A method for producing a pharmaceutical and/or dietetic composition of claim 2, wherein a physiologically effective quantity of the *Lactobacillus* cells are mixed with the physiologically tolerated carrier and prepared for the oral administration.

* * * * *